United States Patent [19]

Herman

[11] Patent Number: 4,955,894
[45] Date of Patent: Sep. 11, 1990

[54] POSTERIOR CAPSULOTOMY KNIFE

[75] Inventor: Wesley K. Herman, Dallas, Tex.

[73] Assignee: Alcon Laboratories, Inc., Fort Worth, Tex.

[21] Appl. No.: 303,016

[22] Filed: Jan. 30, 1989

Related U.S. Application Data

[63] Continuation of Ser. No. 171,234, Mar. 22, 1988, abandoned, which is a continuation of Ser. No. 32,989, Mar. 27, 1987, abandoned, which is a continuation of Ser. No. 874,798, Jun. 13, 1986, abandoned, which is a continuation of Ser. No. 666,558, Oct. 30, 1984, abandoned.

[51] Int. Cl.$^5$ .............................................. A61F 17/32
[52] U.S. Cl. .................................... 606/167; 606/170
[58] Field of Search ............. 128/305, 309, 314, 24 A; 606/107, 167, 166, 170

[56] References Cited

U.S. PATENT DOCUMENTS

| | | | |
|---|---|---|---|
| 1,020,753 | 3/1912 | Ford | 128/314 |
| 1,708,578 | 4/1929 | Hyde | 128/305 |
| 1,749,919 | 3/1930 | Mierley | 128/305 |
| 2,029,495 | 2/1936 | Lowe | 128/305 |
| 2,521,161 | 9/1950 | Grover | 128/305 |
| 3,600,539 | 9/1971 | Miller | 128/314 |
| 4,011,870 | 3/1977 | Goldstein | 128/305 |
| 4,244,060 | 1/1981 | Hoffer | 3/13 |
| 4,298,994 | 11/1981 | Clayman | 3/13 |
| 4,359,053 | 11/1982 | Benjamin | 128/339 |
| 4,412,359 | 11/1983 | Myers | 3/13 |
| 4,527,564 | 7/1985 | Eguchi et al. | 128/339 |

OTHER PUBLICATIONS

The Surgical Armamentarium, American V. Mueller, pp. 510, 513, and 566, 1980.

Primary Examiner—Stephen C. Pellegrino
Assistant Examiner—Kathleen A. Daley
Attorney, Agent, or Firm—Gregg C. Brown

[57] ABSTRACT

A knife for ophthalmic surgery and particularly for posterior capsulotomy procedures comprises a thin, continuously curved shaft having an elongated handle attached at one end thereof. The longitudinal axis of the handle is disposed substantially tangentially to the curved shaft. A blade portion on the opposite end of the shaft terminates in a sharp tip. The shaft tapers from a relatively thick section adjacent the handle to a relatively thin section adjacent the blade portion.

5 Claims, 3 Drawing Sheets

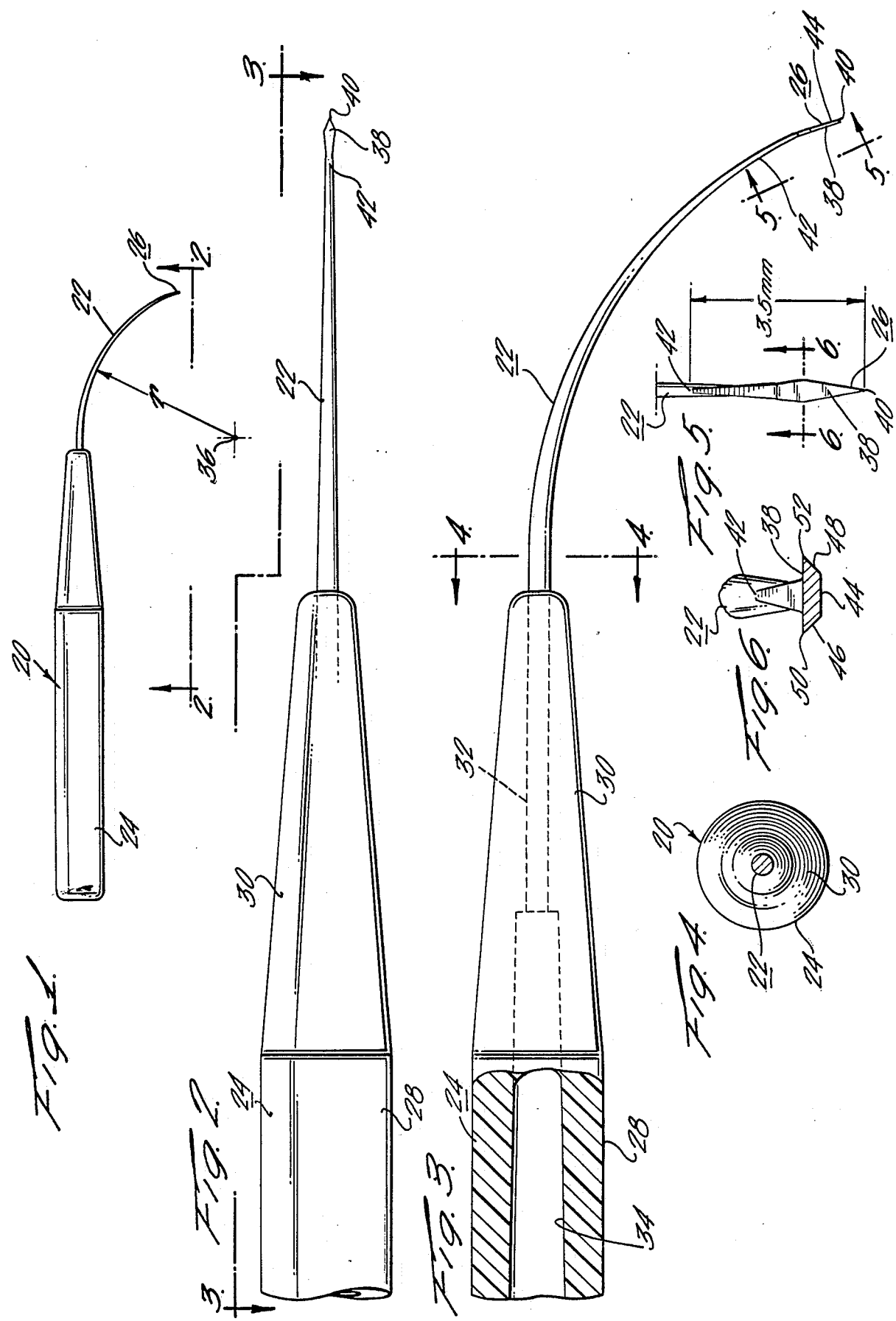

POSTERIOR CAPSULOTOMY KNIFE

This is a continuation of application Ser. No. 171,234, filed Mar. 22, 1988 which is a continuation of Ser. No. 032,989 filed Mar. 27, 1987 (now abandoned) which is a continuation of Ser. No. 874,798 filed June 13, 1986 (now abandoned) which is a continuation of Ser. No. 666,558 filed Oct. 30, 1984 (now abandoned).

BACKGROUND OF THE INVENTION

Large numbers of cataract and lens implant surgical procedures are performed each year, with more than half of these procedures using the extracapsular technique with posterior chamber lens implantation. In this technique, the anterior capsule is partially cut away and the opacified material within the lens capsular bag removed In a growing proportion of these procedures, a posterior chamber intraocular lens is implanted in the ciliary sulcus or in the capsular bag, adjacent the intact posterior capsule. Alternatively, a lens may be implanted in the anterior chamber of the patient's eye. Such implantation may be done concurrently with the cataract extraction or in a later separate procedure.

A problem arising from lens implantation is the difficulty of treating posterior capsule opacification which typically becomes manifest some time after the intraocular lens has been implanted. Although some surgeons have recommended that posterior capsulotomies be performed at the time of the cataract surgery, patients who have had such treatment have suffered a significantly higher incidence of cystoid macular edema as compared to those with capsules left intact at the termination of surgery.

The treatment of posterior capsule opacification after extracapsular surgery is basically of two types, the traditional one being the surgical discising of the posterior capsule, and the more recent involving the use of the Neodymium Yag laser. Although the laser treatment originally showed great promise, there are increasing concerns regarding the safety of the procedure and its effects on the intraocular lens itself. Complications attributed to laser treatment include cystoid macular edema, retinal detachment, lamellar and full thickness macular holes, peripheral retinal tears and hemmorhages, as well as significant lens marking by inadvertently hitting the lens optic or inadvertent cutting of lens haptics with resultant dislocation of the lens. There are also concerns as to liberated free radicals when an intraocular lens or lens haptic is hit with the laser, and recent studies suggest the liberation of cytotoxic agents when the lens optic is hit with the laser.

Because of the above and other concerns as to the safety of the laser treatment, the surgical discission of the posterior capsule is favored by many surgeons. Prior to the present invention, such surgical treatment has been carried out using knives of various types, all of which have shared a common disadvantage in that the configuration of the knife is planar. The approach to the posterior capsule must thus be made by tipping the knife point anteriorly to imbricate the posterior capsule. This cutting motion requires movement by the surgeon of his entire upper arm and elbow in order to incise the capsule. In addition, these knives are very heavy, and if there is minute patient movement, the likelihood of complication is greater.

SUMMARY OF THE INVENTION

The present invention provides a posterior capsulotomy knife characterized by a thin, continuously curved shaft, to one end of which is attached a small elongated handle. The handle is disposed with its longitudinal axis substantially tangentially oriented with respect to said curved shaft. A blade portion on the opposite end of the shaft includes a pair of opposed converging cutting edges which intersect to form a sharp tip. The shaft tapers uniformly from a relatively thick section adjacent said handle to a relatively thin section adjacent said blade portion. The blade portion is visibly distinct from the remainder of said shaft to provide a gauge for locating the point of entry into the eye.

The curvature of the knife shaft permits a very simply surgical procedure in that, following introduction of the knife into the eye, the discission of the opacified posterior capsule can be quickly and accurately completed by a simple rotary motion of the knife handle. The tapered shaft is self-sealing and of a small diameter such that post operative sutures are not required following its removal. The extremely light weight of the knife decreases the possibility of complications should patient movement occur during the procedure.

It is accordingly a primary object of the present invention to provide a surgical knife which simplifies and increases the safety of a surgical posterior capsulotomy procedure.

A further object of the invention is to provide a knife as described, the entry of which inflicts a minimal wound which does not require post operative sutures.

Another object of the invention is to provide a knife as described which minimizes or eliminates vitreous loss during the capsulotomy procedure.

A still further object of the invention is to provide a knife as described which is extremely light in weight and which can be effectively manipulated solely by use of the fingers.

Additional objects and advantages of the invention will be more readily apparent from the following description of a preferred embodiment thereof.

BRIEF DESCRIPTION OF THE DRAWINGS

FIG. 1 is a side view of a posterior capsulotomy knife in accordance with the present invention;

FIG. 2 is an enlarged view taken along line 2—2 of FIG. 1;

FIG. 3 is a view partially broken away and in section taken along line 3—3 of FIG. 2;

FIG. 4 is an enlarged view partly in section taken along line 4—4 of FIG. 3;

FIG. 5 is an enlarged view taken along line 5—5 of FIG. 3;

FIG. 6 is an enlarged view partly in section taken along line 6—6 of FIG. 5;

DESCRIPTION OF THE PREFERRED EMBODIMENT

Figure 7:
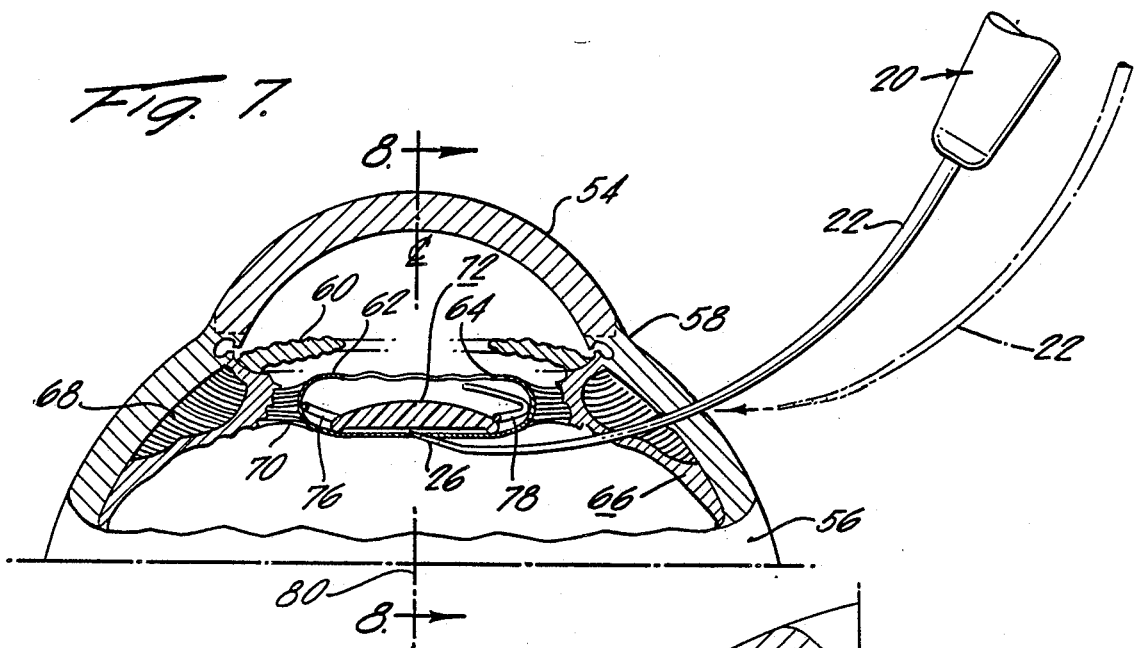
FIG. 7 is a sectional view through a human eye undergoing a posterior capsulectomy, showing the knife of FIGS. 1-6 in position to dicise the posterior capsule.

Referring to the drawings and particularly FIG. 1 thereof, a capsulotomy knife generally designated 20 in accordance with the present invention comprises a thin curved tapered shaft 22 which is attached at one end thereof to a handle 24. The shaft 22 terminates at the end opposite the handle end in a blade portion 26, the details of which are described more specifically below.

Since it is desirable that the knife be extremely light in weight, the handle 24 is of an abbreviated pencil shape, comprising a substantially cylindrical portion 28 and a frusto-conical portion 30 to which the shaft 22 is connected. The handle 24 is preferably made of a lightweight plastic material which is molded onto a straight shank portion 32 of the shaft as shown in FIG. 3. To further lighten the handle, a central bore 34 extending axially therewithin may be provided, which bore may extend the entire length of the cylindrical portion 28 and partially into the frusto-conical portion 30 of the handle. Since the handle is intended only for engagement with and manipulation by the fingers, its length is quite short, on the order of 50 mm. The diameter of the cylindrical portion 28 is preferably about 5 mm.

The shaft 22, which is preferably made of stainless steel, curves, preferably continuously, from adjacent the junction with the handle 24 to the blade portion 26. As shown in FIG. 1, the shaft 22 represents the arc of a circle having a center 36 and a radius r, which in the preferred embodiment is 20 mm. The shaft tapers from adjacent the handle to the blade portion In the preferred embodiment illustrated, the shaft is round in section and tapers from a diameter of approximately 0.875 mm adjacent the handle to approximately 0.2 mm substantially adjacent the blade portion. The preferred length of the shaft 22 from the handle to the tip of the blade portion 26 is approximately 20 mm.

The taper of the shaft 22 allows a self-sealing, generally fluid tight entry of the knife into the eye, thereby preventing unnecessary loss of vitreous fluid during the procedure. The L:D (length to diameter) ratio of the taper is important in this context; it must be sufficient to maintain a seal between the edges of the wound site and the shaft, yet not so great as to require substantially axial force on the knife that will impart additional trauma to the eye. To meet these constraints, an L:D ratio between 20:1 and 40:1 is believed necessary. In the preferred embodiment such ratio is about 30:1. Ideally the taper is substantially continuous over substantially all of its length.

The blade portion 26 of the shaft includes a flat surface 38 facing the center of curvature 36 of the shaft. This surface terminates at the end of the shaft in a sharply pointed tip 40. A transition surface 39 extends from the surface 38 to a point 42 located 3.5 mm from the tip 40 as shown in FIG. 6. As described below, the surfaces 38 and 39 serve as a gauge for locating the point of entrance of the knife into the eye. The blade portion further includes an outer substantially flat surface 44 parallel to the surface 38, and beveled side edges 46 and 48 which intersect at the sharp tip 40. The beveled edges 46 and 48 form, at their intersection with the surface 38 a pair of sharp cutting edges 50 and 52 as shown in FIG. 6.

Referring to FIGS. 7–14, the manner in which the above-described knife is employed to perform a pars plana posterior capsulotomy is illustrated. The human eye shown includes the cornea 54, sclera 56 and limbus 58 at their juncture. These views in addition show the iris 60 as well as the lens 62, the anterior capsule of which has been substantially removed to leave the aperture 64 opening into the posterior chamber.

Figure 8:
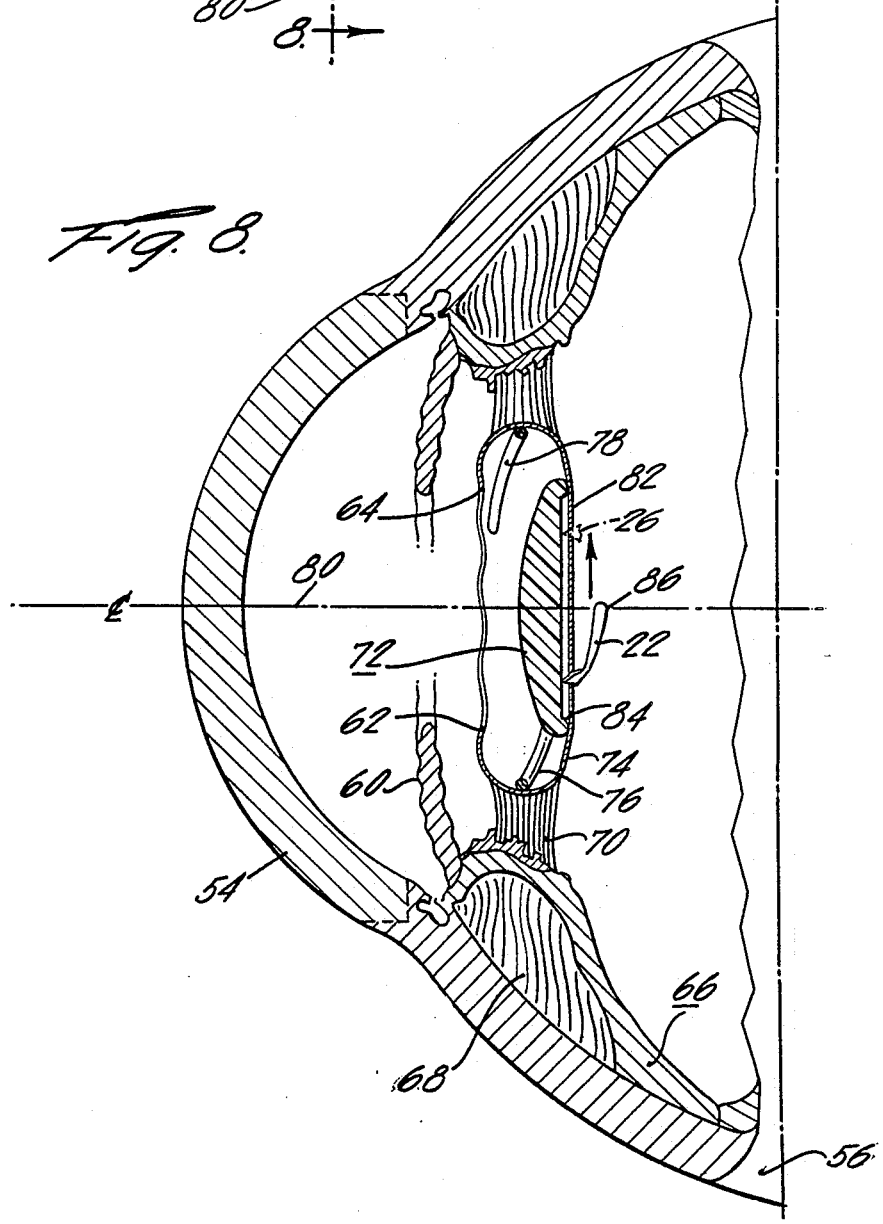
FIG. 8 is an enlarged sectional view taken along line 8—8 of FIG. 7.

The views of FIGS. 7 and 8 are somewhat more detailed, and show in addition to the above-described eye structure, the ciliary body 66 including the ciliary processes 68 as well as the zonules which comprises the suspensory ligaments 70 supporting the lens 62 and connecting it to the ciliary body 66.

The eye illustrated has previously undergone a cataract operation involving the removal of a major portion of the anterior capsule, the removal of the opacified lens nucleus and cortex and the implantation of an intraocular lens (IOL) 72 in the capuslar bag 74. The implanted lens 72 illustrated is held centrally in position within the posterior chamber by a pair of spring loops 76 and 78 which serve not only to centrally locate the lens along the optical axis 80 of the eye, but also to bias the lens rearwardly against the intact posterior capsule 82. The lens 72 illustrated is the type having its convex surface disposed anteriorally with a substantially planar posterior surface bounded by an annular ridge 84. With this type of lens, only the ridge 84 engages the posterior capsule 82, the posterior lens surface being spaced therefrom. Although this type of lens has been developed primarily for laser capsulotomy procedures to minimize damage to the lens, it is particularly well suited to the surgical procedure using the knife of the present invention.

As indicated above, a posterior capsulotomy is necessary when the posterior capsule becomes opacified, which typically occurs some time after the cataract lens and implant procedure. With the implanted lens in place, access to the posterior capsule can be gained only by use of a laser or by surgically discising the capsule from behind the lens by a somewhat awkward frontal approach requiring displacement of the implanted lens. Until the development of the present invention, such surgery has been difficult due to the fact that the plane of the posterior capsule lies somewhat below the preferred entry point for the capsule discising instruments.

Figure 9:
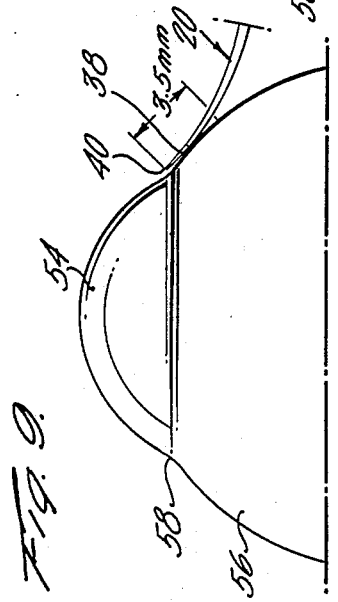
FIG. 9 is a schematic side view of the eye showing the use of the blade portion of the knife as a gauge to locate the point of entrance of the knife into the eye.
Figure 10:
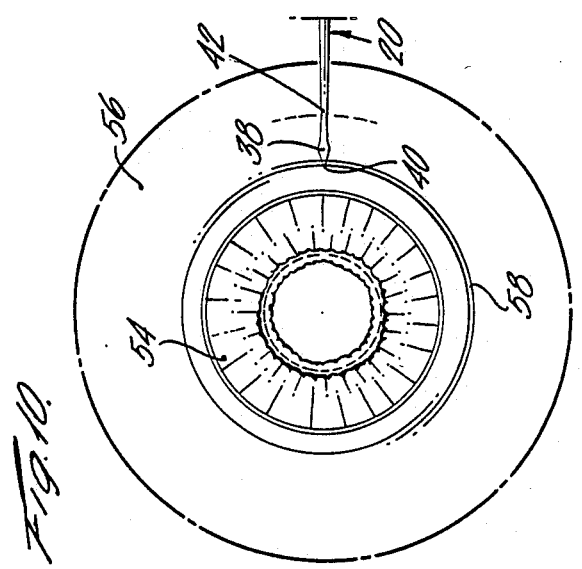
FIG. 10 is a schematic plan view corresponding to FIG. 9.

The capsulotomy procedure using the present knife is a simple, easily performed operation which produces an accurate, controlled discising of the posterior capsule with a minimal amount of trauma to the eye structure. Referring to FIGS. 9 and 10, the procedure is begun by placing the knife 20 in close proximity to the eye in radial alignment with the eye axis and with the point 40 of the knife at the limbus 58 and the surfaces 38 and 39 facing upwardly. The end point 42 of the surface 39 serves to locate the optimal pars plana sclerectomy site which, it is generally agreed, should be 3.5 mm outwardly from the limbus. With this entry site located, the surgeon orients the knife to the position shown in FIG. 7 and introduces the tip 40 into the eye at this site. As the knife is directed into the eye, the curvature of the shaft serves to direct the knife along an arcuate path behind the zonules 70 and the posterior capsule 82.

Figure 11:
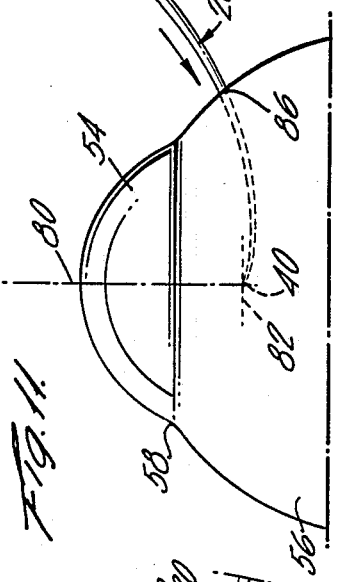
FIG. 11 is a schematic side view similar to FIG. 9 showing the knife inserted into the eye.
Figure 14:
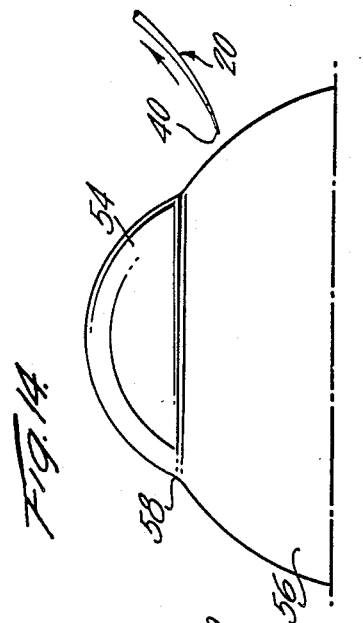
FIG. 14 is a schematic side view of the eye showing the removal of the knife following completion of the procedure.
Figure 12:
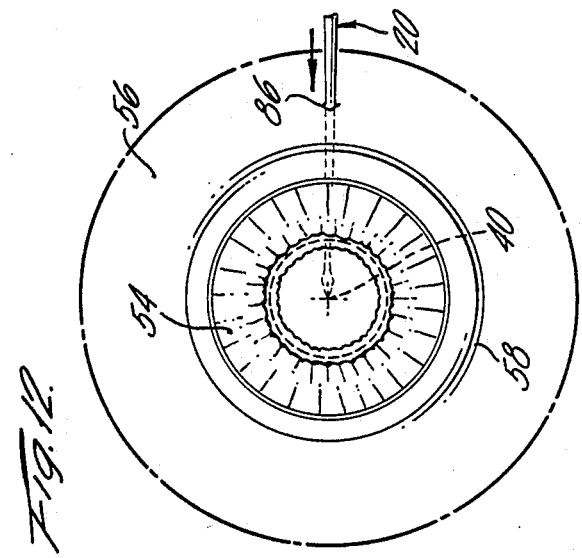
FIG. 12 is a schematic plan view corresponding to FIG. 11 showing the knife centered in the pupil prior to starting the discission of the posterior capsule.
Figure 13:
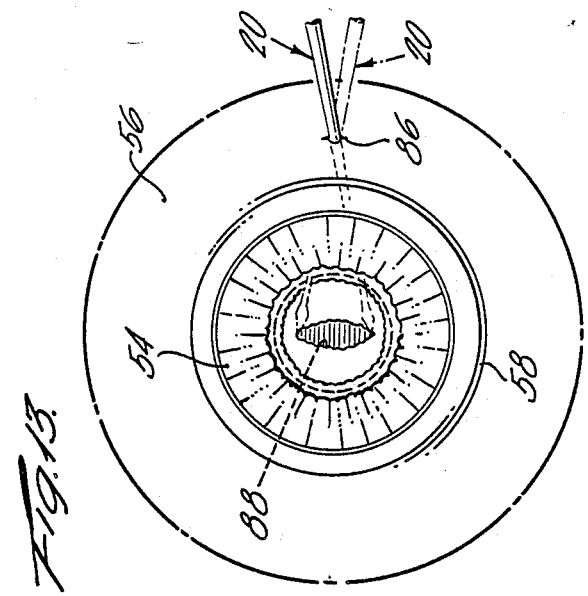
FIG. 13 is a view similar to FIG. 12 showing in broken lines the position of the knife at the beginning of the cutting stroke, and in solid lines the position of the knife following completion of the stroke.

When the knife has been advanced so that approximately one half of the shaft is introduced into the eye, the tip 40 of the blade portion will be visible through the pupil and can be centered at the optical axis of the eye as shown in FIGS. 11 and 12. By means of a simple rotary motion of the handle and without moving the knife shaft axially with respect to the point of entry 86, a cutting stroke of the blade portion 26 through the posterior capsule is effected as shown in FIG. 13. This discission of the capsule creates an elongated aperture 88 therein which is sufficient to restore ample light passage to the retina. The knife is removed from the eye by a simple withdrawal movement as illustrated in FIG. 14.

Because of the tapered shaft configuration, the entry of the knife into the sclera creates a self-sealing wound, thus precluding any possible loss of vitreous. The penetration of the shaft to approximately one half its length (10 mm) produces approximately a 0.5 mm sized opening in the sclera. In view of the small size of the opening and the rotary movement of the knife during the cutting procedure which does not enlarge the opening, postoperative suturing is not required.

The manipulation of the knife during the surgical procedure is carried out with the finger tips and the knife accordingly does not require any arm or elbow motion to produce a cutting action. A simple rotary movement of the knife handle effects the desired cutting stroke as a result of the curved configuration of the shaft.

The present knife may be used in an alternative technique whereby the posterior capsulotomy is performed via an anterior segment approach wherein access to the posterior chamber is obtained through a peripheral iridectomy. In this technique, a clear corneal incision is made thereby precluding any penetration through the pars plana or sclera. The curvature of the present knife shaft provides easy access to the posterior chamber with this technique. Although the knife must penetrate through the zonules during this procedure with the possible resultant breakage of a small number of zonules, this trauma does not have a significant effect on the stability of the capsular system.

The small size and light weight of the present knife is advantageous in permitting its manipulation solely by means of sensitive fingertip movements. The knife is, in fact, so light as to permit its release while inserted in the eye without harmful effect should this be necessary.

Manifestly, changes in details of construction can be effected by those skilled in the art without departing from the invention.

I claim:

1. An ophthalmic surgical knife for performing dicission of the posterior capsule of a human eye, comprising:

a curved shaft having a first end and a second end, said first end comprising a blade portion adapted for cutting the posterior capsule upon reciprocal rotation of said curved shaft along its longitudinal axis, said blade portion including a flat, imperforate surface facing toward the center of curvature of the curved shaft and two opposed cutting edges which converge to form a sharp tip at said first end; and an elongated, cylindrical handle attached to the second end of said curved shaft such that the longitudinal axis of the handle is disposed substantially tangentially with respect to the outer periphery of said curved shaft;

wherein said curved shaft has a circular cross-section from said second end to said blade portion and is continuously tapered from said second end to said blade portion, thereby allowing the shaft to enter the eye in a self-sealing, fluid tight manner which limits the trauma to the eye and prevents the loss of vitreous fluids from the eye.

2. An ophthalmic surgical knife according to claim 1, wherein the curved shaft has a continuous curvature from said second end to said blade portion.

3. An ophthalmic surgical knife according to claim 1, wherein the length to diameter ration of taper of the curved shaft from said second end to said blade portion is between 20:1 to 40:1.

4. An ophthalmic surgical knife according to claim 3, wherein said length to diameter ratio is about 30:1.

5. An ophthalmic surgical knife according to claim 1, wherein the blade portion includes means for locating an optimal injection site, said means comprising a surface on said blade portion which is visibly distinct from the remainder of the blade portion and the curved shaft and has a length adapted for use as a gauge to facilitate location of an optimal injection site.

* * * * *